United States Patent [19]

Sakamoto et al.

[11] Patent Number: 5,399,554
[45] Date of Patent: Mar. 21, 1995

[54] READILY SOLUBLE 2',3'-DIDEOXYINOSINE COMPOSITIONS

[75] Inventors: Kimiyasu Sakamoto; Toshihide Yukawa, both of Kawasaki, Japan

[73] Assignee: Ajinomoto Co., Inc., Tokyo, Japan

[21] Appl. No.: 5,421

[22] Filed: Jan. 19, 1993

Related U.S. Application Data

[63] Continuation of Ser. No. 865,665, Apr. 7, 1992, abandoned, and a continuation of Ser. No. 472,239, Jan. 30, 1990, abandoned.

[30] Foreign Application Priority Data

Feb. 2, 1989 [JP] Japan .................................. 1-24591

[51] Int. Cl.$^6$ ............................................. A61K 31/52
[52] U.S. Cl. ..................... 514/45; 514/964; 424/400; 424/439; 424/457
[58] Field of Search .................... 536/27.14; 562/575; 514/45, 2, 964; 424/400, 439, 457

[56] References Cited

U.S. PATENT DOCUMENTS

| 2,891,945 | 6/1959 | Stark | 536/27.14 |
| 3,937,809 | 2/1976 | Jacobi | 514/47 |
| 4,758,553 | 7/1988 | Ogoshi | 514/47 |
| 4,835,104 | 5/1989 | Yokozeki et al. | 435/822 |
| 5,026,687 | 6/1991 | Yarchoan et al. | 514/45 |
| 5,110,600 | 5/1992 | Green | 514/2 |

OTHER PUBLICATIONS

Chemical Abstracts: vol. 109 (14):115,946z, Anderson et al.

*Primary Examiner*—John W. Rollins
*Assistant Examiner*—James O. Wilson
*Attorney, Agent, or Firm*—Oblon, Spivak, McClelland, Maier & Neustadt

[57] ABSTRACT

A readily soluble 2',3'-dideoxyinosine composition is prepared by combining 80 to 1 parts by weight of a basic amino acid and 20 to 99 parts by weight of 2',3'-dideoxyinosine. The greater solution velocity of this composition improves solubility for therapeutic uses.

3 Claims, No Drawings

READILY SOLUBLE 2',3'-DIDEOXYINOSINE COMPOSITIONS

This application is a Continuation of application Ser. No. 07/865,665, filed on Apr. 7, 1992, now abandoned and a Continuation of application Ser. No. 07/472,239, filed Jan. 30, 1990, now abandoned.

BACKGROUND OF THE INVENTION

1. Field of the Invention

The present invention relates to 2',3'-dideoxyinosine which is rendered readily soluble by adding thereto and mixing therewith basic amino acids, and a process for producing the same. Also within the invention is a process for preparing an aqueous solution of 2',3'-dideoxyinosine. Hereafter 2',3'-dideoxyinosine is sometimes simply referred to as DDI.

2. Discussion of the Background

DDI is used as a drug, e.g., an antiviral agent, in the form of its aqueous solution or in the form of tablets. However, DDI should be dissolved eventually, either outside or inside the human body. DDI has poor solubility in water and this poor solubility causes problems. Therefore, DDI having a high solubility or rapid solubility is desired to eliminate these problems.

SUMMARY OF THE INVENTION

As a result of extensive investigations to solve the solubility problem described above, the present inventors have found that DDI is rendered extremely readily soluble in the presence of basic amino acids. The term "readily soluble" with respect to DDI means that the solubility of DDI in an aqueous medium increases and at the same time, its solution velocity also increases.

DETAILED DESCRIPTION OF THE PREFERRED EMBODIMENTS

The basic amino acid used in the present invention refers to one of arginine, ornithine, lysine and histidine or a mixture of two or more of these amino acids. These amino acids may be used in any of D-form, L-form and DL-form but when DDI is used as a drug, the L-form is, of course, preferred. Furthermore, the basic amino acid may take both the free base form and the salt form. In general, the basic amino acid is commercially available in the form of its acid addition salt, especially in the form of the hydrochloride salt. In the present invention, however, the free base form (Zwitterion form or unionized form) is used. In the case that the acid addition salt is used, the solubility (including parts by weight and solution velocity) of DDI is not improved. Further, there is no difficulty in converting the acid addition salt of the basic amino acid into the free base form. The conversion can be carried out, for example, by use of an ion exchange resin.

Even though it is the same base as the basic amino acid, an inorganic basic salt such as the Na salt, K salt, etc. is not usable in the present invention since it is more difficult to crystallize DDI containing such an inorganic basic salt than DDI containing the basic amino acid.

The ratio of 2',3'-dideoxyinosine and the basic amino acid in the mixture of the readily soluble 2',3'-dideoxyinosine is 80 to 1 part by weight of the basic amino acid based on 20 to 99 parts by weight of 2',3'-dideoxyinosine, preferably 80 to 5 parts by weight of the basic amino acid based on 20 to 95 parts by weight of 2',3'-dideoxyinosine, because the composition must contain DDI and the DDI should be readily soluble.

The present process for producing readily soluble 2',3'-dideoxyinosine which comprises either mixing 2',3'-dideoxyinosine and the basic amino acid and finely grinding the mixture into a powder or mixing previously finely ground 2',3'-dideoxyinosine with previously finely ground basic amino acid is described below. The mixing and finely grinding steps may be appropriately chosen. Furthermore, there is no particular restriction to the degree of fine grinding into the powders. However, in order to increase the solution velocity of the readily soluble 2',3'-dideoxyinosine produced by these processes, it is preferred that the particle size be as small as possible, preferably as small as about 200 mesh.

Another embodiment of the present invention is a process which comprises dissolving 2',3'-dideoxyinosine and the basic amino acid in water, and then (a) subjecting the resulting aqueous solution to a concentrating treatment, (b) adding a poor solvent for 2',3'-dideoxyinosine and the basic amino acid to the aqueous solution, (c) subjecting the resulting aqueous solution to a cooling treatment, and/or (d) first concentrating the solution and then adding the resulting concentrate to a poor solvent for 2',3'-dideoxyinosine and the basic amino acid.

In this process, the charging ratio of DDI and the basic amino acid is preferably 80 to 1 part by weight of the basic amino acid based on 20 to 99 parts by weight of DDI, preferably 80 to 5 parts by weight of the basic amino acid based on 20 to 95 parts by weight of DDI. By adopting the charging ratio in such a range, DDI is crystallized as readily soluble DDI containing a desired amount of the basic amino acid.

The process is carried out, for example, as follows. After mixing DDI with the basic amino acid, water is added to the mixture to dissolve them. The resulting solution is appropriately subjected to one of the following treatments: (a) concentration, (b) addition of a poor solvent, (c) cooling and (d) addition of the concentrate to a poor solvent (or vice versa) or two or more treatments in combination and, if necessary, to other treatments for crystallization. As the poor solvent, a solvent in which the basic amino acid and 2',3'-dideoxyinonsine are substantially insoluble is used. Lower aliphatic alcohols, i.e., methanol, ethanol, isopropyl alcohol, etc., are preferred in view of operability (operability in the treatments). For example, it has been found that when the concentrate is added to isopropyl alcohol (so called reverse addition), the solution velocity is further improved since the shape of precipitated crystals becomes spherical.

The precipitated crystals are separated from the mother liquor by an appropriate method, and dried, e.g., under reduced pressure to give the desired product.

The product produced by this embodiment of the process is superior in its uniformity to the product produced by the first described process which comprises mixing DDI with the basic amino acid and grinding the mixture into fine powders or to the product produced by the process which comprises previously grinding DDI and the basic amino acid into fine powders and then mixing them.

The readily soluble DDI of the present invention may, of course, contain additives used for their intended purpose which do not inhibit the effect of the present invention.

The present invention also includes a process for preparing an aqueous solution of readily soluble 2',3'-dideoxyinosine which comprises dissolving 2',3'-dideoxyinosine in water in the presence of the basic amino acid, and is carried out by adding DDI to an aqueous solution of the basic amino acid or adding a mixture of DDI and the basic amino acid to water. In this case, however, the ratio of 2',3'-dideoxyinosine and the basic amino acid dissolved in the resulting aqueous solution is controlled to 80 to 1 part by weight of the latter based on 20 to 99 parts by weight of the former, preferably 80 to 5 parts by weight of the latter based on 20 to 95 parts by weight of the former. By doing so, a DDI aqueous solution having a high concentration can be readily prepared. Where the DDI aqueous solution is used, e.g., as an antiviral agent, additives which are added to these agents and do not inhibit the effect of the present invention may be added, as in the case of the readily soluble DDI of the present invention described above.

The DDI of the present invention prepared using the solvent precipitation methods and which contains the basic amino acid, has a markedly high solubility and a remarkably improved solution velocity, as compared not only to DDI prepared by the solid mixing processes of the present invention but also to the pure DDI.

Having generally described this invention, a further understanding can be obtained by reference to certain specific examples which are provided herein for purposes of illustration only and are not intended to be limiting unless otherwise specified.

EXAMPLES

Example 1

In 300 ml of water were dissolved 4.72 g of DDI and 3.48 g of L-arginine. The resulting aqueous solution was concentrated to 35 ml and 176 ml of isopropyl alcohol was added to the concentrate, whereby a white precipitate was formed. The precipitate was removed by filtration and dried under reduced pressure.

Analysis by liquid chromatography revealed that the dried product was composed of 3.8 g of DDI and 2.6 g of L-arginine. The thus obtained readily soluble 2',3'-dideoxyinosine had, a solubility of 18.5 g/dl with respect to DDI at 20° C., showing remarkable improvement as compared to the solubility of 2.5 g/dl in the pure DDI system.

With respect to the solution velocity, see Example 5 later described.

Comparative Example

In 300 ml of water were dissolved 5 g of DDI and 0.847 g of sodium hydroxide. The resulting aqueous solution was concentrated to 20 ml and 176 ml of isopropyl alcohol was added to the concentrate, whereby no precipitate was formed.

Example 2

In 300 ml of water were dissolved 3.00 g of DDI and 8.84 g of L-arginine. The resulting aqueous solution was concentrated to 25 ml and 100 ml of isopropyl alcohol was added to the concentrate, whereby a white precipitate was formed. The precipitate was then treated as in Example 1 to give readily soluble DDI composed of 2.4 g of DDI and 7.2 g of L-arginine.

The thus obtained readily soluble 2',3'-dideoxyinosine had a solubility of more than 7 g/dl with respect to DDI at 20° C., showing remarkable improvement as compared to the pure DDI system.

With respect to the solution velocity, see Example 5 later described.

Example 3

In 300 ml of water were dissolved 5 g of DDI and 2.64 g of L-arginine. The resulting aqueous solution was concentrated to 40 ml, whereby a white precipitate was formed. The precipitate was separated by filtration and dried under reduced pressure.

Analysis by liquid chromatography revealed that the dried product was composed of 1.12 g of DDI and 0.12 g of L-arginine. The thus obtained readily soluble 2',3'-dideoxyinosine had a solubility of more than 2.9 g/dl as DDI at 30° C.

With respect to the solution velocity, see Example 5 later described.

Example 4

After 2 g of DDI was mixed with 1.47 g of L-arginine, the mixture was dissolved in 100 ml of water. The resulting aqueous solution was concentrated to 6 ml and the concentrate was poured into 100 ml of ethanol, whereby a white precipitate was formed. The precipitate was then treated as in Example 1 to give readily soluble DDI composed of 1.1 g of DDI and 0.1 g of L-arginine. The thus obtained readily soluble 2',3'-dideoxyinosine had a solubility of more than 2.7 g/dl as DDI at 20° C.

With respect to the solution velocity, see Example 5 later described.

Example 5 (Solution Velocity Test)

The solution velocity of readily soluble DDI prepared by the processes of the present invention was measured. For purpose of comparison, the solution velocity of the pure DDI system was also measured. That is, the time period (seconds) of a sample required for dissolving 1 g of DDI in 100 ml of water at 20° C. with stirring was measured and the time period was identified as solution velocity (1).

Furthermore, a time period (seconds) of a sample required for dissolving 1 g of DDI in 100 ml of phosphate buffer of pH 8 at 20° C. with stirring was measured and the time period was identified as solution velocity (2). The stirring was performed using a magnetic stirrer at one turn/second.

The results are summarized and shown in Table 1.

TABLE 1

| Sample | Example 1 | Example 2 | Example 3 | Example 4 | DDI (control) |
|---|---|---|---|---|---|
| Solution velocity (1) (sec) | 70 | 120 | 140 | 110 | 550 |
| Solution velocity (2) (sec) | 55 | 40 | 110 | 100 | 300 |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A powdered 2′,3′-dideoxyinosine composition consisting essentially of 75–9 wt % arginine and 25–91 wt % 2′,3′-dideoxyinosine, said composition having a solution velocity of 70–140 seconds at 20° C. per 1 gram of said composition in 100 ml water.

2. The composition of claim 1, wherein said composition consists essentially of 75–41 wt % arginine and 25–59 wt % 2′,3′-dideoxyinosine.

3. The composition of claim 1, wherein said composition consists of 75–9 wt % arginine and 25–91 wt % dideoxyinosine.

* * * * *